US010969376B2

(12) United States Patent
Voiron

(10) Patent No.: US 10,969,376 B2
(45) Date of Patent: *Apr. 6, 2021

(54) ELECTRICAL STIMULATION AND MONITORING DEVICE

(71) Applicant: Murata Integrated Passive Solutions, Caen (FR)

(72) Inventor: Frédéric Voiron, Barraux (FR)

(73) Assignee: MURATA INTEGRATED PASSIVE SOLUTIONS, Caen (FR)

(*) Notice: Subject to any disclaimer, the term of this patent is extended or adjusted under 35 U.S.C. 154(b) by 0 days.

This patent is subject to a terminal disclaimer.

(21) Appl. No.: 16/672,881

(22) Filed: Nov. 4, 2019

(65) Prior Publication Data
US 2020/0064327 A1 Feb. 27, 2020

Related U.S. Application Data

(63) Continuation of application No. 16/353,359, filed on Mar. 14, 2019, now Pat. No. 10,488,392, which is a (Continued)

(30) Foreign Application Priority Data

Sep. 19, 2016 (EP) .................................. 16306195

(51) Int. Cl.
*G01R 27/26* (2006.01)
*G01N 33/483* (2006.01)
*H01L 29/94* (2006.01)
*G01N 27/22* (2006.01)
(Continued)

(52) U.S. Cl.
CPC ....... *G01N 33/4836* (2013.01); *G01N 27/228* (2013.01); *H01L 27/0676* (2013.01); *H01L 29/945* (2013.01); *H01L 27/0805* (2013.01)

(58) Field of Classification Search
CPC .... G01N 27/06; G01N 27/22; G01N 27/0676; G01N 27/228; G01N 27/30;
(Continued)

(56) References Cited

U.S. PATENT DOCUMENTS 6,017,775 A * 1/2000 Igel ...................... G01N 27/414
438/142
8,134,222 B2 * 3/2012 Khan ...................... H01L 29/94
257/532
(Continued)

FOREIGN PATENT DOCUMENTS

| JP | 2006094703 A | 4/2006 |
| WO | 2014085727 A1 | 6/2014 |
| WO | 2016124714 A1 | 8/2016 |

OTHER PUBLICATIONS

International Search Report issued for PCT/EP2017/073450, dated Jan. 22, 2018.
(Continued)

*Primary Examiner* — Thang X Le
(74) *Attorney, Agent, or Firm* — Arent Fox LLP

(57) ABSTRACT

An electrical stimulation and monitoring device that includes multiple signal paths that are connected in parallel with each other, and each containing a stimulation or sensing electrode, a DC-blocking capacitor and a stimulation or sensing channel. A semiconductor substrate provided for hosting the DC-blocking capacitors is connected electrically to a DC voltage source through a substrate holding capacitor. Such substrate holding capacitor reduces a blanking time between stimulation and sensing periods, and also reduces cross-couplings between different ones of the signal paths while all the DC-blocking capacitors are provided on one and same semiconductor substrate.

20 Claims, 4 Drawing Sheets

Related U.S. Application Data continuation of application No. PCT/EP2017/073450, filed on Sep. 18, 2017.

(51) Int. Cl.
*H01L 27/06* (2006.01)
*H01L 27/08* (2006.01)

(58) Field of Classification Search
CPC .. G01N 27/414; G01N 27/416; G01N 33/483; G01N 33/4836
See application file for complete search history.

(56) References Cited

U.S. PATENT DOCUMENTS

| | | | |
|---|---|---|---|
| 2003/0228848 A1* | 12/2003 | Escoffier | H01L 27/0251 455/91 |
| 2009/0273356 A1 | 11/2009 | Pampin et al. | |
| 2010/0060349 A1 | 3/2010 | Etter et al. | |
| 2011/0018094 A1* | 1/2011 | Chapman | H01L 29/945 257/532 |
| 2012/0001235 A1* | 1/2012 | Fife | G01N 27/414 257/253 |
| 2014/0036399 A1* | 2/2014 | Ory | H01L 23/62 361/56 |
| 2014/0083872 A1 | 3/2014 | Fuerst et al. | |
| 2014/0084295 A1* | 3/2014 | Hirler | H01L 29/407 257/67 |
| 2014/0093881 A1 | 4/2014 | Sugnet et al. | |
| 2017/0227533 A1 | 8/2017 | Lin et al. | |

OTHER PUBLICATIONS

Written Opinion of the International Searching Authority issued for PCT/EP2017/073450, dated Jan. 22, 2018.

* cited by examiner

ELECTRICAL STIMULATION AND MONITORING DEVICE

CROSS REFERENCE TO RELATED APPLICATIONS

The present application is a continuation of U.S. patent application Ser. No. 16/353,359, filed on Mar. 14, 2019, which is a continuation of PCT/EP2017/073450 filed Sep. 18, 2017, which claims priority to European Patent Application No. 16306195.5, filed Sep. 19, 2016, the entire contents of each of which are incorporated herein by reference.

TECHNICAL FIELD

The invention relates to an electrical stimulation and monitoring device, suitable in particular for analyzing biological tissues.

BACKGROUND

Electrical stimulation and response monitoring is implemented for analyzing a medium such as biological tissues. For avoiding that the medium is altered by any DC voltage component which may appear between electrodes applied to this medium, and then may cause unwanted electrolysis processes within the medium, each stimulation sequence is comprised of a first time period for injecting electrical charges into the medium, and a second time period for draining from the medium a charge amount which equals that of the charges injected. The second time period of the stimulation immediately follows the first one. For ensuring that the electrical charge amounts which are injected into and drained from the medium are equal, the electrical stimulation is performed through a DC-blocking capacitor.

Commonly, a set of electrodes is built as a braid and arranged so that all the electrodes are simultaneously in contact with the medium. Each one of these electrodes is intended to produce a stimulation sequence as described above, or to collect an electrical response from the medium. For this reason, these electrodes are called stimulation or sensing electrodes. It is then essential that no cross-coupling occurs between different ones of the electrodes during stimulation and also during response monitoring, which would be due to electronic circuits connected to the electrodes.

Each electrode may be either a stimulation electrode or a sensing electrode, or may have alternately the stimulation function or the sensing function depending on a stimulation channel or a sensing channel being currently connected to this electrode. Each electrode is thus connected to a stimulation or sensing channel which is dedicated to this electrode through a DC-blocking capacitor, separately from the other electrodes. Hence a set of capacitors is to be provided for the whole set of electrodes, such that one capacitor is connected electrically between one of the electrodes and the corresponding stimulation or sensing channel.

Up to now, all the DC-blocking capacitors of an electrical stimulation and monitoring device which has multiple stimulation or sensing electrodes are provided as discrete components. These discrete capacitors are mounted on a substrate such as a printed circuit board or a ceramic substrate.

Then it would be cost-effective and allow denser integration to provide all the DC-blocking capacitors which are necessary for all the stimulation or sensing electrodes in the form of an integrated circuit which is produced from one semiconductor substrate. Such electrical stimulation and monitoring device would then comprise: a semiconductor substrate of a first conduction type, which is provided with a set of separated wells all having a second conduction type, the first and second conduction types being opposite so that each well forms a respective embedded diode at a boundary between this well and a bulk portion of the substrate having the first conductivity type; a set of capacitor structures which are each accommodated within one of the wells separately from the other capacitor structures, each capacitor structure having a first electrode, a second electrode and a layer portion of an electrically insulating material, the first electrode being formed by the well which is dedicated to this capacitor structure, and the layer portion of insulating material being arranged between the first and second electrodes; a set of stimulation or sensing electrodes which are each connected to the first electrode of one of the capacitor structures; and a set of stimulation or sensing channels which are each connected to the second electrode of one of the capacitor structures, and each comprising a current source for injecting a stimulation current into one of the stimulation or sensing electrodes through one of the capacitor structures which is connected serially between the stimulation or sensing channel and the stimulation or sensing electrode, or comprising a sensing circuit for allowing monitoring of a voltage response collected by one of the stimulation or sensing electrodes, and detected by the sensing circuit through the capacitor structure which is connected serially between the stimulation or sensing electrode and the stimulation or sensing channel.

According to such design, the device is comprised of a set of signal paths each comprised of one stimulation or sensing electrode, one capacitor structure and one stimulation or sensing channel which are connected serially in this order. The capacitor structure has the DC-blocking function mentioned earlier. Electrical insulation between the capacitor structures, within the integrated circuit, is provided by the diodes which are formed at the boundary between each well which accommodates one of the capacitor structures and the bulk portion of the substrate. But because such well diodes are not actually perfect, they have junction capacitors and leakage currents which cause cross-couplings between separate ones of the signal paths. Then stimulation which is intended to be applied to the analyzed medium though a selected one of the electrodes also produces unwanted stimulation through another one of the electrodes. This results in unwanted voltage build-up across some parts of the medium.

Generally, after one stimulation sequence has been applied to the medium through one of the electrodes, a blanking time is necessary before starting sensing the response from the medium, because a residual voltage which has been caused within the medium by the stimulation sequence needs to relax. Indeed such residual voltage may saturate an amplifier which is implemented within the sensing channels, thus making it impossible to sense the true response of the medium which corresponds to biological activity before the residual voltage has relaxed. Blanking time thus limits the response which can be collected, and also limits the number of stimulation and sensing cycles which can be performed within a fixed duration.

When the device is used for therapy purpose, a number of successive stimulation sequences are to be applied at a frequency which is also limited by the blanking time. Indeed, the medium has to relax after each stimulation sequence for avoiding that the residual voltages which are caused by the sequences accumulate and produce an overall voltage runaway within the medium.

Therefore, it is an issue for both uses of electrical stimulation and monitoring devices to shorten the blanking time.

Additionally, if a failure such as dielectric breakdown occurs in one of the capacitor structures of the above device which is based on a semiconductor substrate for hosting the DC-blocking capacitors, a resistive conduction path which passes through the medium appears. Then, an unwanted DC current which would flow along such path can damage the medium. Therefore, it is desirable to have a security dielectric isolation in addition to the capacitor structure within each loop formed by one of the signal paths and a reference voltage branch which leads to a reference electrode also applied to the medium.

SUMMARY OF THE INVENTION

In view of the foregoing, objects of the present invention are for improving electrical stimulation and monitoring devices that are based on semiconductor substrates for hosting the DC-blocking capacitors, for addressing at least one of the following issues: reducing cross-couplings between the stimulation and sensing electrodes, shortening the blanking time and providing a security isolation efficient in case of DC-blocking capacitor failure.

Accordingly, in view of these objectives, the invention proposes an electrical stimulation and monitoring device which is based on a semiconductor substrate provided with wells and capacitor structures as recited above, but which comprises a further capacitor, called substrate holding capacitor. This substrate holding capacitor has a first electrode which is electrically connected to the substrate bulk portion, and a second electrode which is electrically connected for receiving a reference DC voltage set with respect to a first terminal common to the stimulation or sensing channels, and also common to a reference electrode intended to be applied on the medium to be analyzed through electrical stimulation and monitoring, when the stimulation or sensing electrodes are also applied to this medium.

When the connection of the first electrode of the substrate holding capacitor to the substrate bulk portion is close to one of the wells, it reduces electrical interferences which could affect the capacitor structure accommodated within this well, in particular interferences that are caused by other ones of the capacitor structures. In this way, cross-couplings involving the capacitor structure which is located close to the connection of the substrate holding capacitor to the substrate bulk portion are reduced. For reducing in this way the cross-couplings which could affect any one of the capacitor structures, the connection of the first electrode of the substrate holding capacitor to the substrate bulk portion may have a distributed configuration, with parts of the connection to the substrate bulk portion which are close to each one of the wells.

In addition, the substrate holding capacitor is connected serially with the capacitors structures having the DC-blocking function, towards the reference electrode. This reduces the effective capacity value for each signal path completed with the reference voltage branch. Voltage relaxation of the medium is then more rapid, so that the blanking time can be reduced.

Finally, a dielectric layer of the substrate holding capacitor provides an additional dielectric isolation along each signal path completed with the reference voltage branch. This additional dielectric isolation may be effective as a security if one of the capacitor structures having the DC-blocking function encounters failure and becomes short circuit.

In preferred embodiments of the invention, the first electrode of the substrate holding capacitor may be connected to the substrate bulk portion through at least one contact area which is located at the substrate surface and provided to the substrate bulk portion outside all of the wells. Such contact area has the first conduction type with a conductivity value which is higher than a conductivity value of the substrate bulk portion, but lower than a conductivity value of the wells. In addition, each contact area may have a point-contact design, or advantageously a line-shaped contact design in which the contact area is parallel and close to an edge of at least one of the wells but outside this well, or even more advantageously a loop-shaped contact design in which the contact area surrounds at least one of the wells outside this well, in a projection into a substrate surface. The line-shaped and the loop-shaped contact designs provide an increased reduction of the cross-couplings, in a greater extent for the loop-shaped contact design. Most preferably, each well which contains one of the capacitor structures connected between one of the stimulation or sensing electrodes and one of the stimulation or sensing channels, may be surrounded by one contact area outside this well.

According to another exemplary aspect of the invention, the semiconductor substrate may further comprise a shallow doping blanket at a surface of the substrate. Such shallow doping blanket has the first conduction type and another conductivity value which is higher than the conductivity value of the substrate bulk portion. It extends from the substrate surface into the substrate bulk portion, and surrounds each well close against this well, and optionally also extends from each contact area into the substrate bulk portion. Providing such shallow doping blanket allows tuning the breakdown voltage and the leakage current of the well diodes. Optionally, the shallow doping blanket may also form the substrate doping within each contact area, or join each contact area.

If the first conduction type is p, then the second conduction type is n, and the device is adapted so that the reference DC voltage which is received by the second electrode of the substrate holding capacitor is zero or negative. The reference voltage is generally measured with respect to the reference electrode to be applied to the medium at the same time as the stimulation or sensing electrodes.

Conversely, if the first conduction type is n, then the second conduction type is p, and the device is adapted so that the reference DC voltage which is received by the second electrode of the substrate holding capacitor is positive, again with respect to the reference electrode.

Generally, the reference DC voltage may be comprised between −40 V and +40 V, preferably between −30 V and +30 V.

In additional exemplary embodiments of the invention, the substrate holding capacitor may be comprised of an electronic component which is separate from the semiconductor substrate. But preferably, the substrate holding capacitor may be comprised alternatively of a dedicated one of the capacitor structures, which is contained in one of the wells provided in the semiconductor substrate. For such latter embodiments, the first electrode of the capacitor structure which is dedicated to the substrate holding capacitor forms the first electrode of the substrate holding capacitor. It is then connected electrically to the substrate bulk portion through a metal-like electrically conducting element which is arranged above the semiconductor substrate.

Simultaneously, the second electrode of the capacitor structure which is dedicated to the substrate holding capacitor forms the second electrode of the substrate holding capacitor.

The invention device may further comprise a switch which connects the second electrode of the substrate holding capacitor to a second terminal arranged for supplying the reference DC voltage. In this way, the switch has an open state which is suitable for stimulation periods during which stimulation is applied to the medium, and a closed state which is suitable for sensing periods during which the response voltage is collected from the medium.

In an exemplary aspect, at least one of the capacitor structures can be of trench capacitor type. Accordingly, the capacitor structure may comprise at least one trench arranged in the well which accommodates this capacitor structure. It may further comprise the layer portion of electrically insulating material and a portion of an electrically conducting material. The well outside the trench forms the first electrode of the capacitor structure, and the portion of electrically conducting material, which is stacked on the layer portion of electrically insulating material at least within the trench, forms the second electrode of the capacitor structure.

BRIEF DESCRIPTION OF THE DRAWINGS

It is noted that for clarity sake, element sizes which appear in these figures do not correspond to actual dimensions or dimension ratios. Also, same reference numbers or signs which are indicated in different ones of these figures denote identical elements of elements with identical function.

DETAILED DESCRIPTION

Figure 1:
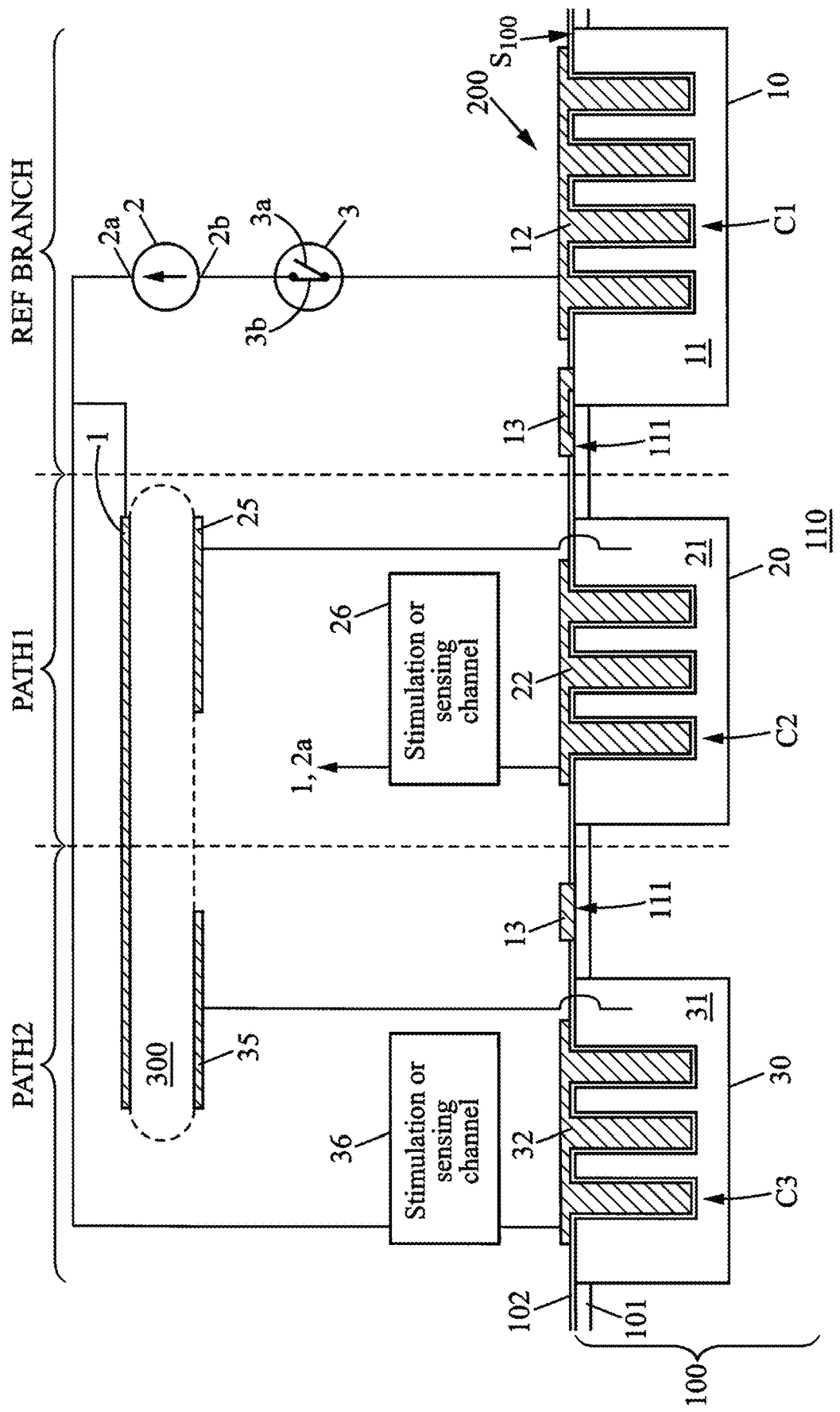
FIG. 1 is a schematic view of a device according to an exemplary embodiment of the invention, including a cross-sectional view of an integrated circuit which is part of the device.

According to FIG. 1, an electrical stimulation and monitoring device comprises an integrated circuit 200 and several signal paths. For clarity sake of the figure, only two signal paths are represented, with respective labels PATH1 and PATH2, but the device may comprise any number of signal paths all arranged in parallel, for example 16 or 32 signal paths. Each signal path comprises separately from the other signal paths: a stimulating or sensing electrode, a capacitor structure forming DC-blocking capacitor, and a stimulation or sensing channel. For example, PATH1 comprises the stimulating or sensing electrode 25, the capacitor structure C2 and the stimulation or sensing channel 26. Similarly, PATH2 comprises the stimulating or sensing electrode 35, the capacitor structure C3 and the stimulation or sensing channel 36.

The device further comprises a reference voltage branch, labelled REF BRANCH, which comprises a reference electrode 1, a DC voltage source 2, and an electrical connection for connecting the DC voltage source 2 to the semiconductor substrate of the integrated circuit 200. The reference electrode 1 is connected to a first terminal 2a of the DC voltage source 2, and a second terminal 2b of the DC voltage source 2 is connected to a bulk portion of the semiconductor substrate. According to the invention, the connection from the second terminal 2b of the DC voltage source 2 leads to the bulk portion of the semiconductor substrate through a dedicated capacitor, called substrate holding capacitor, and optionally also through a switch 3. Put another way, the electrical connection from the second terminal 2b of the DC voltage source 2 to the bulk portion of the semiconductor substrate contains a substrate holding capacitor and optionally a switch, serially connected between the second terminal 2b and the substrate bulk portion.

The capacitor structures are now described at first according to a preferred embodiment of the invention, and the function and advantages of the substrate holding capacitor will be described later.

The semiconductor substrate, labelled 100, for example a silicon substrate, and preferably of p conduction type, has a top substrate surface $S_{100}$. Wells are provided in a well-known manner within the substrate 100, for creating separate volumes of n conduction type. Each well is dedicated to accommodate a separate capacitor structure, which may be of trench capacitor structure type. For example, the well 20 accommodates the capacitor structure C2, which has been formed from trenches edged into parts of the well 20. The capacitor structure C2 also comprises a part of an electrically insulating layer 102 and a portion of an electrically conducting material. The part of the insulating layer 102 and the portion of conducting material are stacked within and between the trenches etched in the well 20. According to this structure, the well 20 outside the trenches forms the first capacitor electrode 21 of the capacitor structure C2, the stacked portion of electrically conducting material forms the second capacitor electrode 22 of the capacitor structure C2, and the part of the insulating layer 102 forms the capacitor dielectric. Similarly for the capacitor structure C3 which is accommodated in the well 30, the well 30 forms the first capacitor electrode 31 outside the trenches, another portion of electrically conducting material forms the second capacitor electrode 32 and another part of the insulating layer 102 which is located between the first capacitor electrode 31 and the second capacitor electrode 32 forms the capacitor dielectric. Again for the capacitor structure C1 which is accommodated in the well 10: the well 10 outside the trenches forms the first capacitor electrode 11, still another portion of electrically conducting material forms the second capacitor electrode 12, and still another part of the insulating layer 102 which is located between the first capacitor electrode 11 and the second capacitor electrode 12 forms the capacitor dielectric. All the capacitor structures formed in the semiconductor substrate 100 may have the trench structure just described, possibly with different dimensions depending on the capacitor value desired for each one. The insulating layer 102 may be of silica ($SiO_2$) and the second electrodes 12, 22 and 32 may be of polysilicon.

In a well-known manner, each one of these capacitor structures is electrically isolated from the bulk portion 110 of the substrate 100 by the diode which is formed at the boundary between the corresponding well and the substrate bulk portion 110. "Isolated" means in this situation that the well diode is in blocked state whatever the voltages that exist at the capacitor electrodes within the well. Also in a known manner, such well diode has a non-zero junction capacitor value and a non-zero leakage current value. It is then possible to tune these junction capacitor and leakage current values of the well diodes by arranging a shallow doping blanket 101 just below the top surface $S_{100}$ of the substrate 100. Such shallow doping blanket may extend at least down to about 0.2 μm (micrometre), possibly down to 0.4 μm, from the top surface $S_{100}$ into the substrate 100. It is of the same conduction type as the substrate bulk portion 110, namely p in the embodiment currently described. The shallow doping blanket 101 overlaps each well 10, 20, 30 and extends laterally beyond its peripheral boundary, so that part of the shallow doping blanket surrounds each well while being closed against this latter. In this way, the shallow doping blanket 101 contains the well diode just below the substrate surface $S_{100}$, so that the doping concentration within the shallow doping blanket 101 allows tuning the junction capacitor and the leakage current of the well diode. Doping concentrations are typically: $10^{13}$ to $5·10^{15}$ boron atoms per cm³ (cubic centimetre) within the substrate bulk portion 110, more than $10^{20}$ phosphorus atoms per cm³ within the wells 10, 20, 30 close to the substrate surface $S_{100}$, and $10^{16}$ to $5·10^{17}$ boron atoms per cm³ within the shallow doping blanket 101.

As already mentioned, one of the capacitor structures is dedicated to each signal path of the device for producing the DC-blocking function for this signal path. In this way, the first capacitor electrode 21 of the capacitor structure C2 is connected electrically to the stimulation or sensing electrode 25, and the second capacitor electrode 22 of the same capacitor structure C2 is connected electrically to the stimulation or sensing channel 26. Similarly for the capacitor structure C3: its first capacitor electrode 31 is connected to the stimulation or sensing electrode 35 and its second capacitor electrode 32 is connected to the stimulation or sensing channel 36.

Again in a well-known manner, each stimulation or sensing channel 26, 36 includes a current source when it is operated as a stimulation channel, or includes a sensing circuit when it is operated as a sensing channel. Reference terminals of all the stimulation or sensing channels of the device are electrically connected to the reference electrode 1 and to the first terminal 2a of the DC voltage source 2, separately from signal terminals of the stimulation or sensing channels 26, 36 which are connected to the second capacitor electrodes 22, 32 of the capacitor structures C2, C3 used for signal paths.

Reference number 300 denotes the medium to be analyzed using the described device. It is inserted between the reference electrode 1 on one hand, and the stimulation or sensing electrodes 25, 35 on the other hand.

The capacitor structure C1 which is accommodated in the well 10 may be dedicated to the substrate holding capacitor, now also called C1 for short. To this end, the second capacitor electrode 12 is connected electrically through metal wiring and optionally also through the switch 3 to the second terminal 2b of the DC voltage source 2. The first capacitor electrode 11 is connected electrically to the bulk portion 110 of the substrate 100. For the embodiment currently described with the substrate conduction type being p, the DC voltage source 2 produces a negative voltage value, possibly zero, at the second terminal 2b with respect to the first voltage terminal 2a. For other embodiments where the substrate conduction type is n, the DC voltage source 2 produces a positive voltage value at the second terminal 2b with respect to the first voltage terminal 2a. Put another way and generally for the invention, the substrate holding capacitor is connected electrically to the cathode side of each one of well diodes of the wells which accommodate capacitor structures connected to one of the stimulation or sensing electrodes when the semiconductor substrate is of n-type. Conversely, it is connected to the anode side of these well diodes when the semiconductor substrate is of p-type. Hence, the DC voltage source 2 biases the substrate bulk portion 110 for ensuring that the well diodes are in blocked state. Generally, the voltage as produced by the DC voltage source 2 is between −40 V (volts) and +40 V. It has been called reference DC voltage in the general part of this description. When this voltage is zero, for p-type semiconductor substrate, the second capacitor electrode 12 of the substrate holding capacitor C1 may be connected directly to the reference electrode 1 and the reference terminals of the stimulation or sensing channels 26, 36, again possibly through the switch 3 but without DC voltage source.

For connecting the first capacitor electrode 11 of the substrate holding capacitor C1 to the substrate bulk portion 110, a contact area 111 is formed at the substrate top face $S_{100}$, and the doping concentration of the substrate bulk portion 110 is locally increased below the contact area 111, while maintaining the same conduction type as that of the substrate bulk portion 110. The increase in the doping concentration below the contact area 111 may be formed by part of the shallow doping blanket 101. Alternatively or in combination, it may be formed by an additional doping step with doping concentration possibly higher than that of the shallow doping blanket. A metal-like electrically conducting element 13 then bridges between the first capacitor electrode 11 of the substrate holding capacitor C1 and the contact area 111 provided with increased doping. The conducting element 13 may pertain to a metallization layer which is dedicated to wiring and arranged above the substrate surface $S_{100}$.

Figure 2:
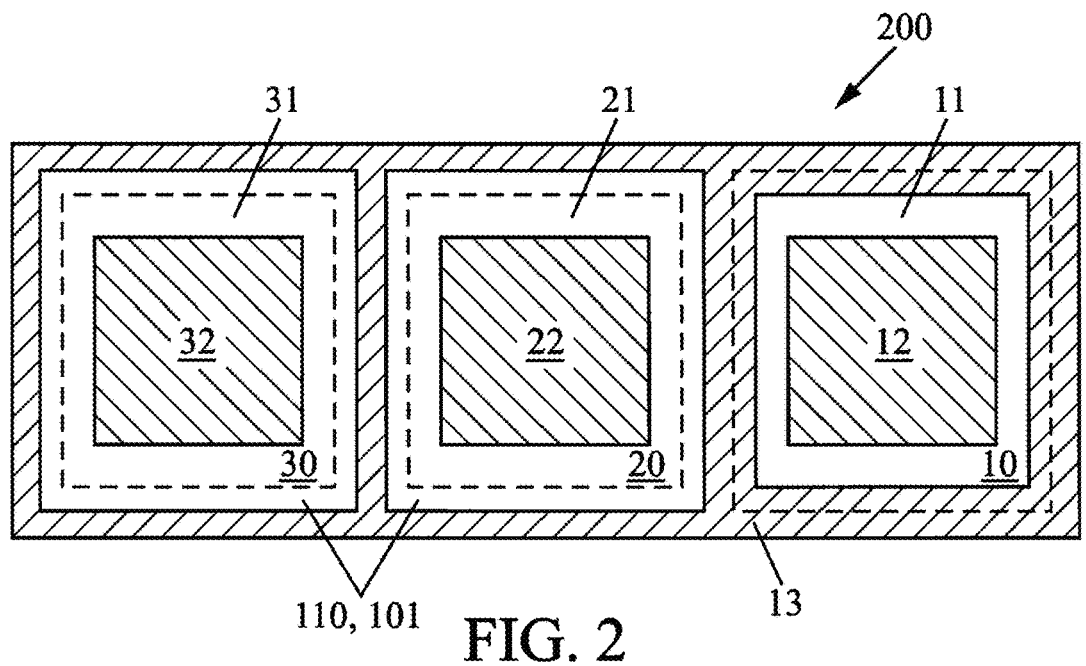
FIG. 2 is part of a top view of the integrated circuit shown in FIG. 1.

It is especially advantageous that the contact area 111 is close to each well of the capacitor structures which are dedicated to the signal paths, namely close to the wells 20 and 30 represented in FIG. 1, while remaining outside these wells. According to a first design possible for the contact area 111, this latter may comprise a plurality of separate point-shaped contact areas, which are distributed around the wells dedicated to the signal paths, and close to the peripheral boundaries of these wells. The point-shaped contact areas are all connected electrically to each other, for example through appropriate metal wirings which are arranged in at least one metallization layer above the substrate top face $S_{100}$. Alternatively but preferably, a second design possible for the contact area 111 may comprise a plurality of separate line-shaped contact areas, which are distributed parallel to and close to the well boundaries of the wells dedicated to the signal paths, but outside these wells, and which are all connected to each other. Alternatively again but most preferably, a loop-shaped design for the contact area 111 may comprise a closed-loop strip which surrounds externally each well dedicated to one of the signal paths close to the peripheral boundary of this well. FIG. 2 illustrates such most preferred design, with the conducting element 13 being further astride the boundary of the well 10 which accommodates the substrate holding capacitor C1.

The optional switch 3 may be provided for limiting the effectiveness of the voltage as produced by the DC voltage source 2 to time periods dedicated to sensing the response from the medium 300. Accordingly, the switch 3 is in open state during stimulation time periods as denoted by the reference sign 3a in FIG. 1, and in closed state 3b during sensing time periods, each sensing time period following a stimulation time period.

Figure 3:
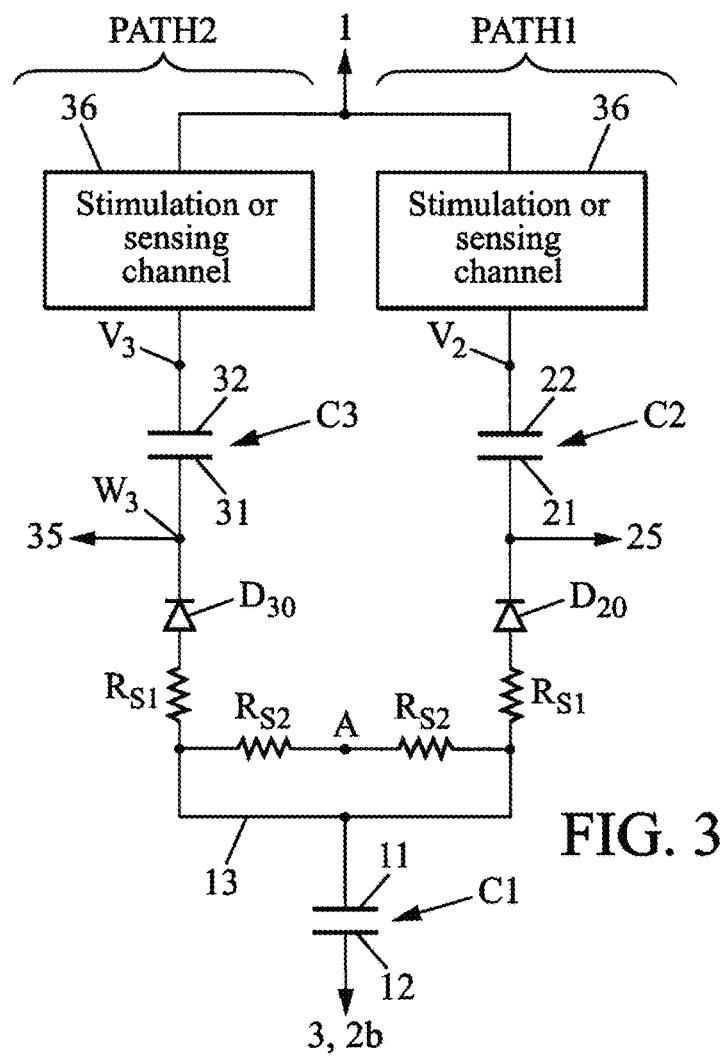
FIG. 3 is an electrical diagram equivalent to the device of FIG. 1.

The diagram of FIG. 3 is an electrical arrangement which is equivalent to the device of FIG. 1. Thus, $D_{20}$ and $D_{30}$ denote respectively the well diodes of the wells 20 and 30, and $R_{S1}$ and $R_{S2}$ denote the serially-connected resistor values which are effective within the substrate 100 between each one of the first capacitor electrodes 21, 31 and a reference point A of the substrate bulk portion 110. Typically, $R_{S1}$ equals 1 ohm and $R_{S2}$ equals 5 kilo ohm, this latter value being due to the low doping concentration of the substrate bulk portion 110. Typically, the reference point A may be located close to a back face of the substrate 100.

For devices which would not implement any substrate holding capacitor while the DC-blocking capacitors are hosted by a common semiconductor substrate, the reference voltage branch REF BRANCH would be connected directly to the substrate bulk portion 110 at point A. Then each signal path PATH1, PATH2 would exhibit a serial resistance value of the order of 5 kilo ohm. In addition, this resistance value allows a significant DC current to pass through the medium 300 if one of the capacitor structures dedicated to DC-blocking function fails.

But in a device as currently described in accordance with the present invention, each signal path PATH1, PATH2 exhibits a residual serial resistance value of the order of 1 ohm only. This very low value is mainly due to the short distance between each well 20, 30 and the contact area 111. But unwanted DC current through the medium 300 is now blocked by the substrate holding capacitor C1.

A possible value for each one of the capacitor structures C2, C3 which are dedicated to the DC-blocking function within the signal paths may be 1.5 nF (nanofarad).

An exemplary value for the capacitor structure C1 which is dedicated to the substrate holding capacitor may be 10 nF (nanofarad). Generally, the benefit of the substrate holding capacitor as provided by the invention is larger for the substrates which exhibit high impedance and for media to be analyzed which exhibit low capacitance value for their interactions with the electrodes.

The shallow doping blanket 101 may be adjusted for the well diodes $D_{20}$ and $D_{30}$ to have each a junction capacitor of about 10 pF (picofarad) and a leakage current of about 50 nanoampere.

Diagrams of FIGS. 4a-4c and 5a-5c have been obtained with p-type silicon substrate and the DC voltage being zero for the reference voltage source 2. Therefore, the second capacitor electrode 12 of the substrate holding capacitor C1 is grounded during the sensing period. These figures display time variations of the voltages existing at the points $V_2$, $V_3$ and $W_3$ as indicated in FIG. 3, assuming that the stimulation or sensing channel 26 is used as a stimulation channel and the stimulation or sensing channel 36 is used as sensing channel. Point $V_2$ belongs to the signal path PATH1 used for stimulation, and points $V_3$ and $W_3$ both belong to the signal path PATH2 used for response monitoring. In all these diagrams, x-axis indicates time in seconds and y-axis indicates voltage values in volts. An electrical model has been used for the medium 300 as described in the article entitled "Brain impedance characteristics of deep brain stimulation electrodes in vitro and in vivo", Xuefeng F. Wei and Warren M. Grill, J. Neural Eng., August 2009, 6(4): 046008. For simplicity, voltage curves corresponding to voltage existing at the points $V_2$, $V_3$ and $W_3$ have been labelled $V_2$, $V_3$ and $W_3$ respectively in the diagrams of FIGS. 4a-4c and 5a-5c.

Figure 4A:
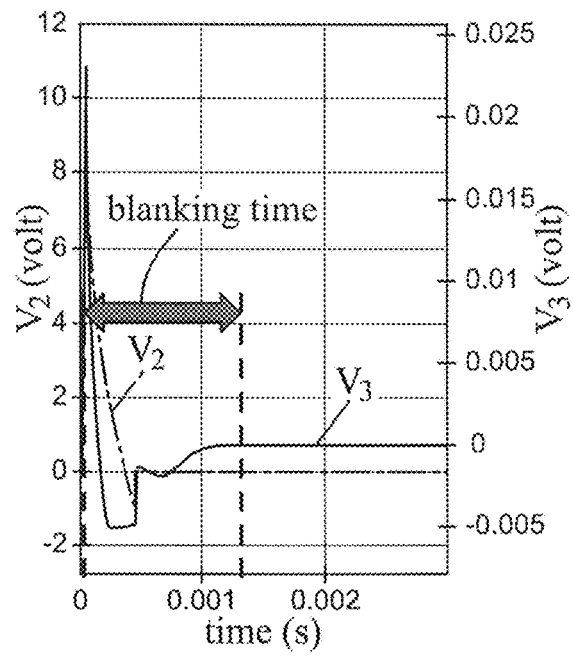
FIGS. 4a to 4c are time-diagrams which illustrate a reduction in a blanking time according to the exemplary embodiment of the invention.
Figure 4B:
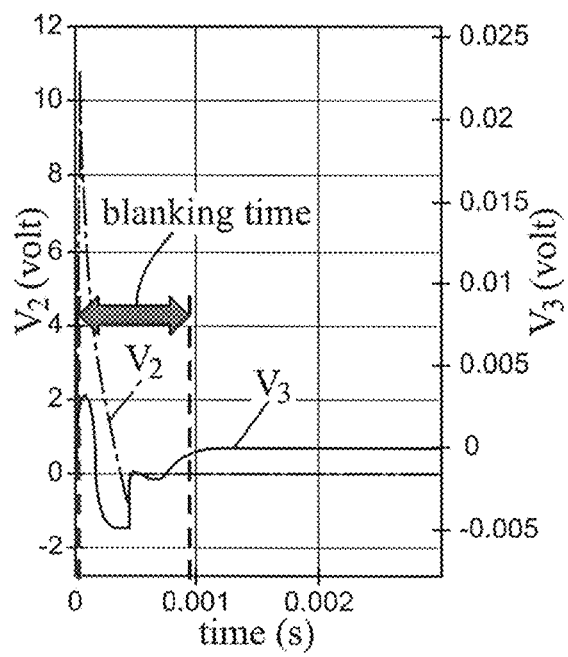
Figure 4C:
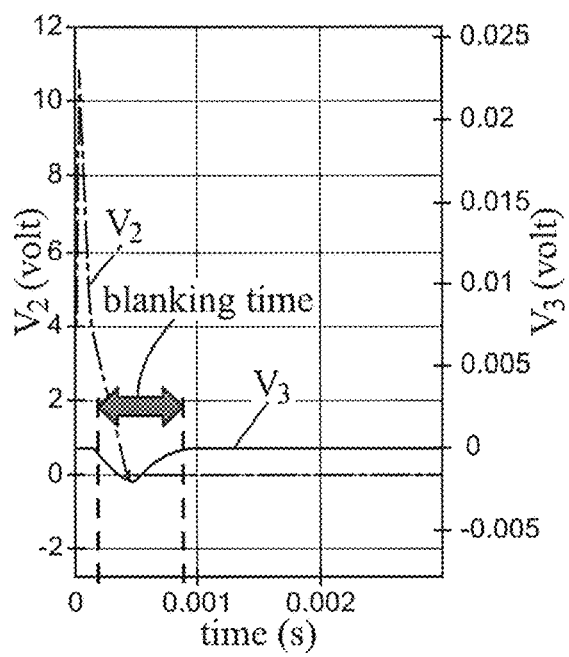

In the diagrams of FIGS. 4a-4c, the curves $V_2$ which are the same in the three diagrams and refer to the y-axes lying on the left side of the diagrams, correspond to a time-integration of the charge injection-and-suction which is implemented for stimulation. The curves $V_3$ which refer to the y-axes lying on the right side of the diagrams, correspond to relaxation. FIG. 4a corresponds to the case of no substrate holding capacitor implemented (substrate grounded at point A as indicated in FIG. 3). FIG. 4b corresponds to the substrate holding capacitor C1 equalling 1 nF, and FIG. 4c when C1 equals 100 nF. The relaxation duration, also called blanking time, is about 0.0013 s (second) without substrate holding capacitor (FIG. 4a), about 0.0009 s for the 1 nF substrate holding capacitor (FIG. 4b), and about 0.0007 s for the 100 nF substrate holding capacitor (FIG. 4c). Therefore, using a substrate holding capacitor of 100 nF produces a reduction of about 40% in the blanking time.

Figure 5A:
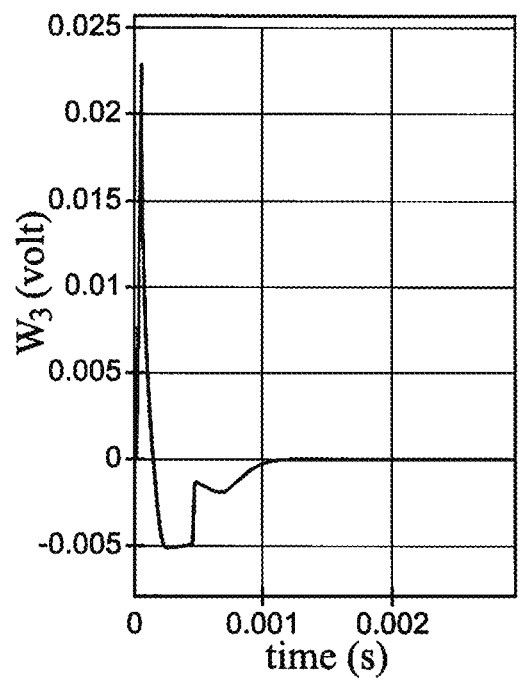
FIGS. 5a to 5c are time-diagrams which illustrate a reduction in an electrode cross-coupling according to the exemplary embodiment of the invention.
Figure 5B:
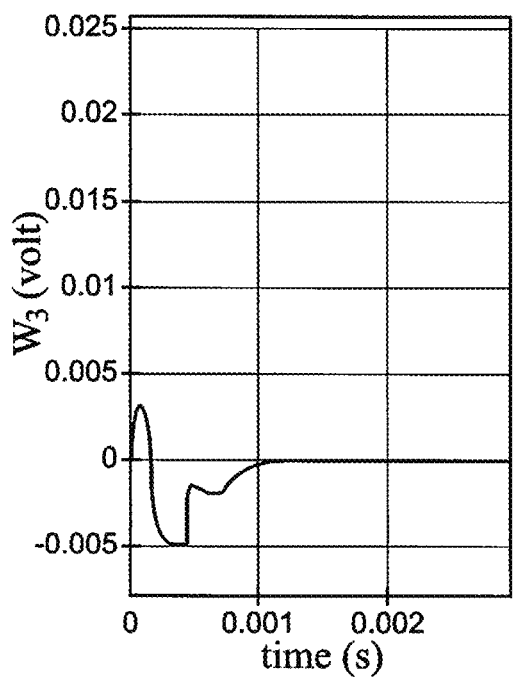
Figure 5C:
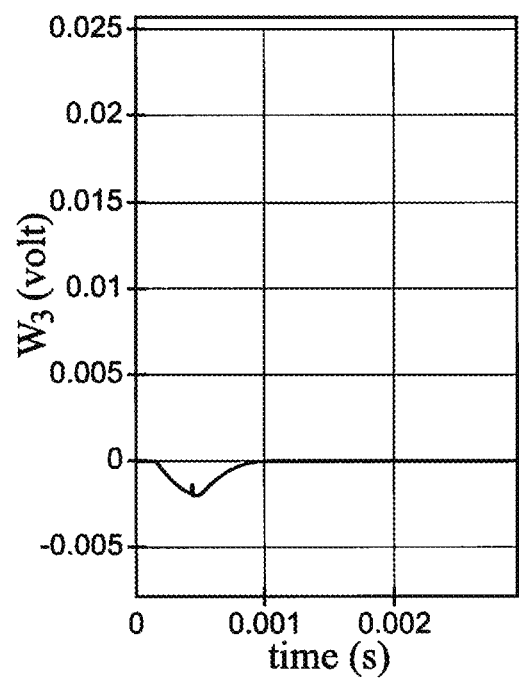

FIGS. 5a-5c illustrate changes in the cross-coupling which occurs when stimulation is produced again through the signal path PATH1, but the voltage exhibited is now that collected at the sensing electrode 35 of the signal path PATH2 (see location of point $W_3$ in FIG. 3). FIG. 5a corresponds to the case of no substrate holding capacitor implemented, as for FIG. 4a. FIGS. 5b and 5c correspond to the substrate holding capacitor C1 equalling 1 nF (FIG. 5b) and 100 nF (FIG. 5c). Actually, the curves $W_3$ of FIGS. 5a-5c are very similar to those labelled $V_3$ in FIGS. 4a-4c because the impedance of the medium 300 is much higher than the value of the DC-blocking capacitor C3. FIGS. 5a-5c show that the cross-coupling is reduced in a great extent by implementing a substrate holding capacitor (FIGS. 5b and 5c compared to FIG. 5a), and the cross-coupling decreases when increasing the value of the substrate holding capacitor (FIG. 5c compared to FIG. 5b).

Finally, it is reminded that the substrate holding capacitor is not necessarily part of the integrated circuit which contains the DC-blocking capacitor structures dedicated to the signal paths. Indeed, as a variant of the embodiment described in detail above, the substrate holding capacitor may be comprised of an electronic component separate from the integrated circuit, and connected thereto so as to recover the serial connection of the substrate holding capacitor between the substrate bulk portion and the DC voltage source.

Also, the number of signal paths which are provided in parallel with each other may be any, without limitation while usual invention embodiments may contain between 8 and 32 signal paths.

The invention claimed is:

1. A device comprising:
   a substrate of a first conduction type and that includes a plurality of wells of a second conduction type with each well forming a respective embedded diode at a boundary between the respective well and a bulk portion of the substrate;
   a plurality of capacitor structures each disposed within a respective well of the plurality wells and having a first electrode, a second electrode, and a layer of an electrically insulating material, the first electrode being formed by the respective well in which the capacitor structure is disposed, and the layer of insulating material being disposed between the first and second electrodes; and
   a plurality of stimulation or sensing electrodes that are each connected to a respective first electrode of a respective capacitor structure of the plurality of capacitor structures.

2. The device of claim 1, further comprising a substrate holding capacitor having a first electrode electrically connected to the bulk portion of the substrate and a second electrode configured to receive a reference DC voltage.

3. The device of claim 2, further comprising a plurality of simulation or sensing channels each connected to a respective second electrode of a respective capacitor structure of the plurality of capacitor structures.

4. The device of claim 3, wherein each simulation or sensing channel comprises:
a current source configured to inject a stimulation current into a respective stimulation or sensing electrode of the plurality of stimulation or sensing electrodes through the respective capacitor structure connected to the respective stimulation or sensing electrode; or
a sensing circuit configured to monitor a voltage response collected by the respective stimulation or sensing electrode of the plurality of stimulation or sensing electrodes and detected by the sensing circuit through the respective capacitor structure connected to the respective stimulation or sensing electrode.

5. The device of claim 3, wherein the reference DC voltage is set with respect to a terminal common to the stimulation or sensing channels and to a reference electrode, and where the reference electrode is configured to be applied together with the stimulation or sensing electrodes to a medium for analysis thereof.

6. The device of claim 2, wherein the first electrode of the substrate holding capacitor is connected to the bulk portion of the substrate through a contact area having a conductivity value that is higher than a conductivity value of the bulk portion of the substrate and lower than a conductivity value of the plurality of wells.

7. The device of claim 6, wherein the contact area has a point-contact design, or a line-shaped contact design in which the contact area is parallel and adjacent to an edge of a respective well of the plurality of wells and outside the respective well, or a loop-shaped contact design in which the contact area surrounds the respective well, in a projection into a substrate surface.

8. The device of claim 1, wherein the substrate further comprises a shallow doping blanket at a surface of the substrate.

9. The device of claim 8, wherein the shallow doping blanket comprises the first conduction type and has a conductivity value that is higher than a conductivity value of the bulk portion of the substrate.

10. The device of claim 2, wherein the first conduction type is p-type, the second conduction type is n-type, and the reference DC voltage received by the second electrode of the substrate holding capacitor is zero or negative.

11. The device of claim 2, wherein the first conduction type is n-type, the second conduction type is p-type, and the reference DC voltage received by the second electrode of the substrate holding capacitor is positive.

12. The device of claim 2, wherein the substrate holding capacitor comprises a dedicated capacitor structure of the plurality of capacitor structures.

13. The device of claim 2, further comprising a switch configured to connect the second electrode of the substrate holding capacitor to a terminal for supplying the reference DC voltage.

14. The device of claim 13, wherein the switch is configured to be in an open state when a stimulation is applied to a medium under analysis and in a closed state when a response voltage is collected from the medium.

15. The device of claim 1, wherein at least one capacitor structure of the plurality of capacitor structures includes a trench capacitor.

16. The device of claim 15, wherein the at least one capacitor structure comprises a portion of an electrically conducting material that forms the second electrode of the at least one capacitor structure.

17. The device of claim 16, wherein the portion of the electrically conducting material is stacked on the layer of electrically insulating material of the at least one capacitor structure at least within a trench of the trench capacitor.

18. A device comprising:
a substrate of a first conduction type and that includes a plurality of wells of a second conduction type with each well forming a respective embedded diode at a boundary between the respective well and a bulk portion of the substrate;
a plurality of capacitor structures each disposed within a respective well of the plurality wells and having a first electrode, a second electrode, and a layer of an electrically insulating material, with the first electrode being formed by the respective well in which the capacitor structure is disposed, and the layer of insulating material being disposed between the first and second electrodes; and
a substrate holding capacitor having a first electrode electrically connected to the bulk portion of the substrate and a second electrode configured to receive a reference DC voltage.

19. The device of claim 18, further comprising a plurality of stimulation or sensing electrodes each connected to a respective first electrode of a respective capacitor structure of the plurality of capacitor structures.

20. The device of claim 18, further comprising a plurality of simulation or sensing channels each connected to a respective second electrode of a respective capacitor structure of the plurality of capacitor structures.

* * * * *